(12) United States Patent
Feldtman

(10) Patent No.: US 9,381,319 B2
(45) Date of Patent: *Jul. 5, 2016

(54) VASCULAR DELIVERY DEVICES

(71) Applicant: Robert Feldtman, Dallas, TX (US)

(72) Inventor: Robert Feldtman, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/684,620

(22) Filed: Apr. 13, 2015

(65) Prior Publication Data

US 2015/0265804 A1    Sep. 24, 2015

Related U.S. Application Data

(63) Continuation of application No. 13/269,996, filed on Oct. 10, 2011, now Pat. No. 9,005,266.

(51) Int. Cl.
*A61M 25/00* (2006.01)
*A61M 25/09* (2006.01)

(52) U.S. Cl.
CPC ....... *A61M 25/0074* (2013.01); *A61M 25/0082* (2013.01); *A61M 25/09* (2013.01); *A61M 2025/0079* (2013.01); *A61M 2025/09125* (2013.01)

(58) Field of Classification Search
CPC ............. A61M 25/0074; A61M 25/0082; A61M 25/09; A61M 2025/0079; A61M 2025/09125
USPC .......... 623/1.11, 1.12, 1.23; 606/200, 194, 606/198; 604/158, 164.01–164.04, 164.07, 604/164.12, 164.13, 165.01, 165.02, 604/165.03, 167.06

See application file for complete search history.

(56) References Cited

U.S. PATENT DOCUMENTS

| | | | | |
|---|---|---|---|---|
| 9,005,266 | B2* | 4/2015 | Feldtman | A61M 25/0074 623/1.11 |
| 2003/0036788 | A1* | 2/2003 | Coe | A61N 1/056 607/119 |
| 2007/0149898 | A1* | 6/2007 | Inderbitzen | A61M 25/09 600/585 |
| 2008/0114390 | A1* | 5/2008 | Guinan | A61M 25/09041 606/194 |
| 2009/0105653 | A1* | 4/2009 | Spenser | A61F 2/013 604/164.13 |
| 2010/0298922 | A1* | 11/2010 | Thornton | A61M 25/09 623/1.11 |
| 2011/0196396 | A1* | 8/2011 | Richter | A61B 17/22012 606/159 |

* cited by examiner

*Primary Examiner* — Katrina Stransky
(74) *Attorney, Agent, or Firm* — The Elliott Law Firm; Douglas H. Elliott; Sarah J. Kelly

(57) ABSTRACT

A vascular method is disclosed comprising introducing a first flexible wire into a blood vessel, wherein the blood vessel has a first vessel end and a second vessel end and wherein the first flexible wire has a first end and a second end, sliding an angiotip along the first flexible wire in a direction away from the first end of the wire and toward the second end of the wire, frictionally engaging the first flexible wire with the angiotip, and pulling the first flexible wire through the blood vessel in the direction of the second vessel end, wherein the pulling of the first flexible wire pulls the angiotip through the blood vessel in the direction of the second vessel end.

4 Claims, 6 Drawing Sheets

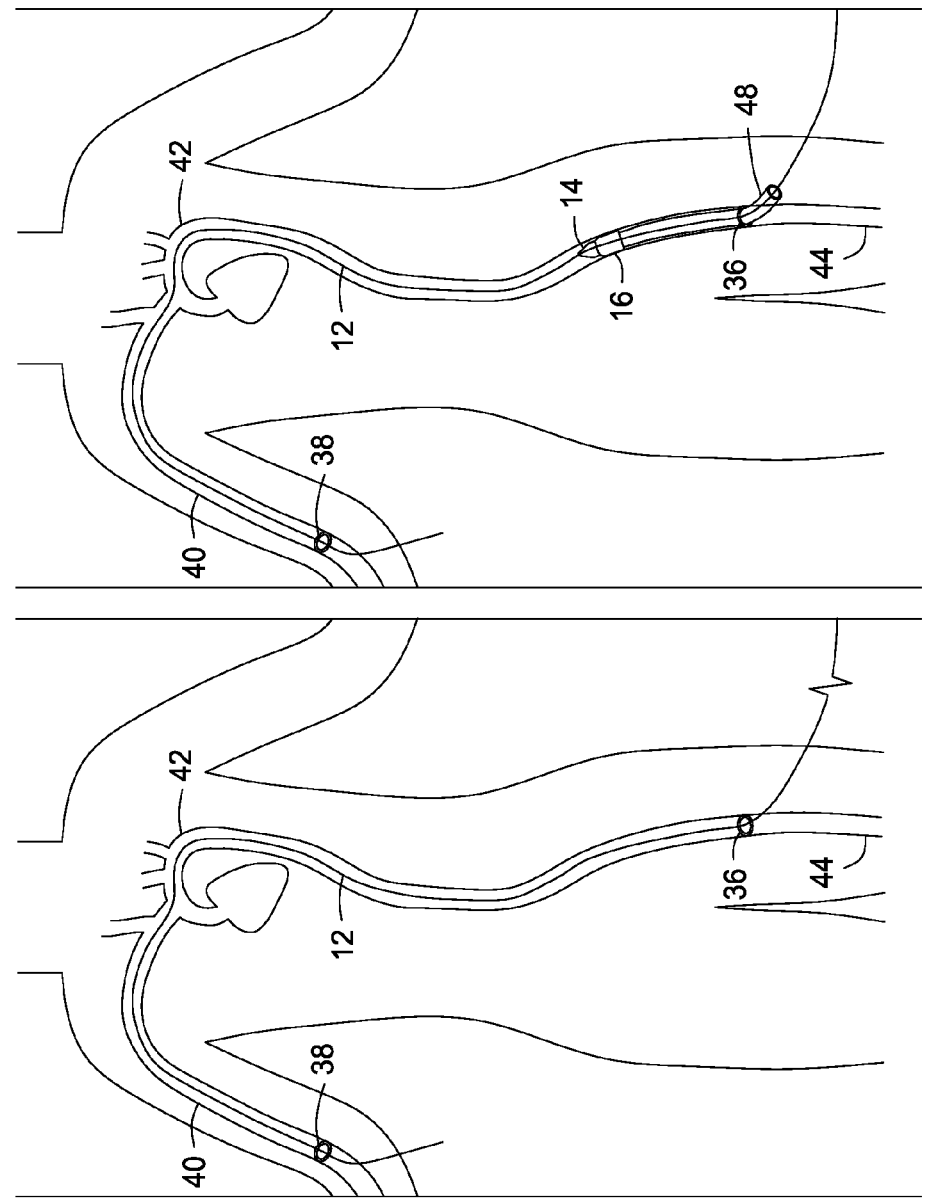

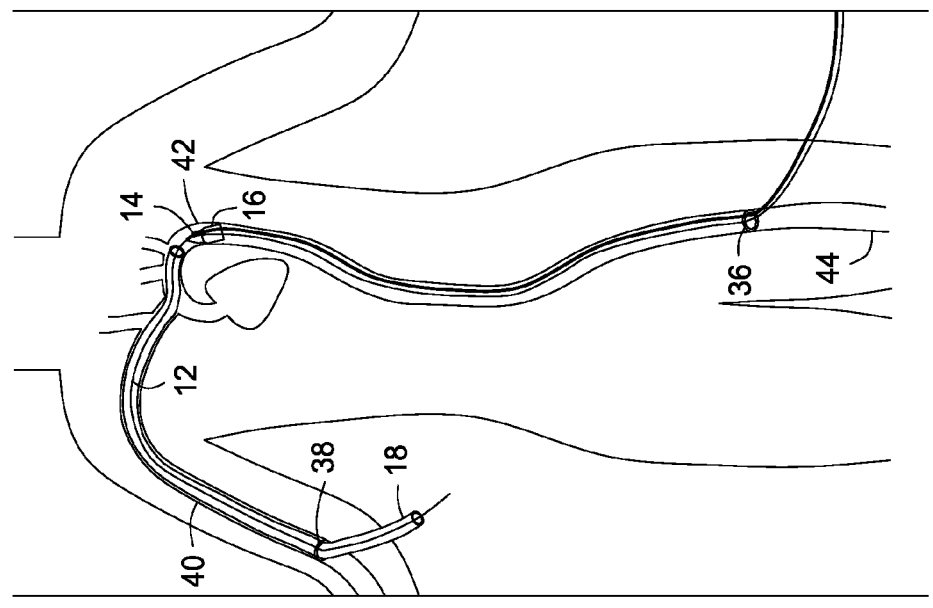
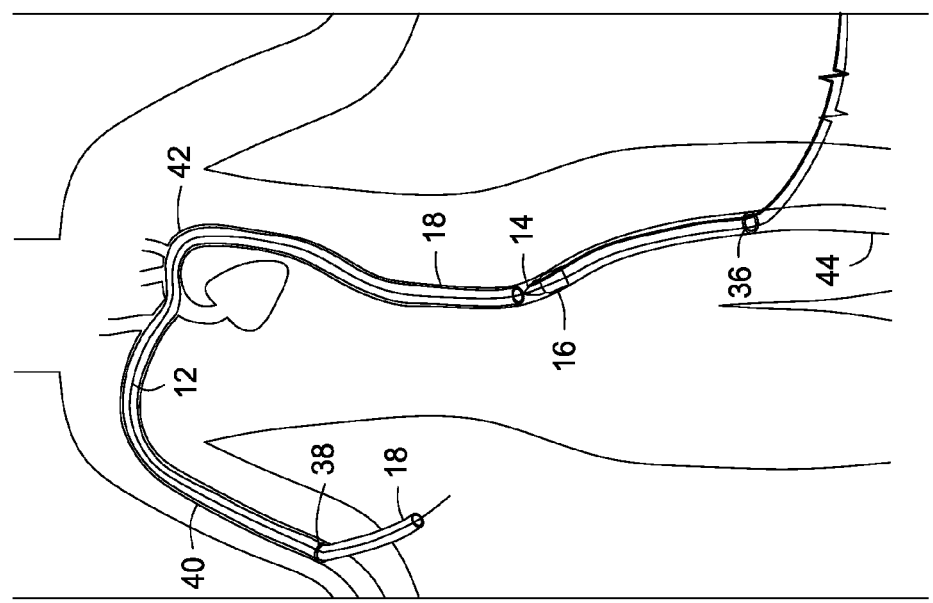

US 9,381,319 B2

VASCULAR DELIVERY DEVICES

This application is a continuation of, and claims benefit of, U.S. application Ser. No. 13/269,996, filed Oct. 10, 2011, now U.S. Pat. No. 9,005,266, which is hereby incorporated by reference in its entirety.

BACKGROUND

1. Field of Inventions

The field of this application and any resulting patent is vascular delivery methods.

2. Description of Related Art

This application and any patent issuing therefrom relates to vascular delivery methods including methods for delivering cardiovascular devices. Endovascular surgery has revolutionized the treatment of cardiovascular disease. Most cardiovascular disease is now treated with devices which are pushed into place over a wire. Patients now enjoy minimally invasive repair of cardiovascular disease without painful incisions. However, extreme vessel tortuosity and stenosis can be dangerous in the placement of ever larger devices into blood vessels.

Various methods and devices have been proposed and utilized to deliver a cardiovascular device to a target location, including the methods and devices disclosed in the patents appearing on the face of this patent. However, these methods and devices lack all the steps or features of the methods and devices covered by the patent claims below, and the methods and structures claimed in this issued patent solve many of the problems found in many of the methods and structures in those earlier patents, have unpredictable benefits, and overcome shortcomings inherent in those earlier methods and structures.

SUMMARY

One or more specific embodiments disclosed herein includes a vascular method comprising (including): introducing a first flexible wire into a blood vessel, wherein the blood vessel has a first vessel end and a second vessel end and wherein the first flexible wire has a first end and a second end, sliding an angiotip along the first flexible wire in a direction away from the first end of the wire and toward the second end of the wire, frictionally engaging the first flexible wire with the angiotip, and pulling the first flexible wire through the blood vessel in the direction of the second vessel end, wherein the pulling of the first flexible wire pulls the angiotip through the blood vessel in the direction of the second vessel end.

One or more specific embodiments disclosed herein includes a surgical method preferably comprising: introducing a first flexible wire into a blood vessel, wherein the blood vessel has a first vessel end and a second vessel end and wherein the first flexible wire has a first end and a second end; sliding an angiotip along the first flexible wire in a direction away from the first end of the wire and toward the second end of the wire; applying a brake to the first flexible wire; and pulling the first flexible wire through the blood vessel in the direction of the second vessel end, wherein the pulling of the first flexible wire pulls the angiotip through the blood vessel in the direction of the second vessel end.

One or more specific embodiments disclosed herein includes a surgical device preferably comprising: a first flexible wire; an angiotip comprising an inner cavity; and a brake capable of limiting the movement of the first flexible wire in the longitudinal directions within the inner cavity of the angiotip.

BRIEF DESCRIPTION OF THE DRAWINGS

FIG. 9A is a simplified top view of a body with a guide wire inserted into a blood vessel.

FIG. 9B is a simplified top view of a body with an angiotip and device partially advanced along a guide wire within a blood vessel.

FIG. 9C is a simplified top view of a body with a locking wire inserted through a blood vessel to an angiotip.

FIG. 9D is a simplified top view of a body depicting further advancement of an angiotip and device due to engagement of the angiotip and guide wire and movement of the guide wire and angiotip such that the angiotip is advanced to a target site.

DETAILED DESCRIPTION

1. Introduction

Figure 2B:
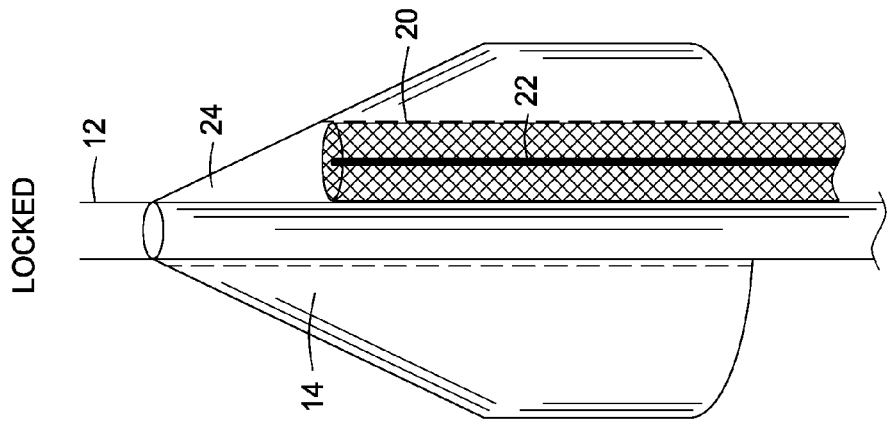
FIG. 2B is a cut-away side view of an angiotip and other elements of FIG. 1 in the locked position.

A detailed description will now be provided. The purpose of this detailed description, which includes the drawings, is to satisfy the statutory requirements of 35 U.S.C §112. For example, the detailed description includes disclosure of the inventor's best mode of practicing the inventions, a description of the inventions, and sufficient information that would enable a person having ordinary skill in the art to make and use the inventions referenced in the claims. In all the figures, like elements are indicated by like reference numerals regardless of the view in which the elements appear. The figures are intended to assist the description and to provide a visual representation of certain aspects of the subject matter described herein. Those figures are not drawn to scale, nor are they intended to show all the structural details of the pulling methods and apparatuses, nor to limit the scope of the claims.

Each of the appended claims defines a separate invention, which for infringement purposes is recognized as including equivalents of the various elements or limitations specified in the claims. Depending on the context, all references below to the "invention" may in some cases refer to certain specific embodiments only. In other cases, it will be recognized that references to the "invention" will refer to the subject matter recited in one or more, but not necessarily all, of the claims. Each of the inventions will now be described in greater detail below, including specific embodiments, versions, and examples, but the inventions are not limited to these embodiments, versions, or examples, which are included to enable a person having ordinary skill in the art to make and use the inventions, when the information in this patent is combined with available information and technology. Various terms as used herein are defined below, and the definitions should be adopted when construing the claims that include those terms, except to the extent a different meaning is given within the specification or in express representations to the Patent and Trademark Office (PTO). To the extent a term used in a claim is not defined below, or in representations to the PTO, it should be given the broadest definition persons in the pertinent art have given that term as reflected in printed publications, dictionaries, and issued patents.

2. Selected Definitions

Certain claims include one or more of the following terms, which, as used herein, are expressly defined as follows.

The term "angiotip" (ANGIOTIP is claimed to be a trademark of Endologix, Inc.) is broadly defined herein as a housing comprising at least one inner cavity capable of containing at least a portion of a wire and at least one opening at one end (e.g. distal end) for the wire. The housing is preferably made of plastic and has a proximal lateral face and a distal lateral face that are substantially perpendicular to the parallel portions of the longitudinal sides of the housing. The housing may be beveled longitudinally on the distal end, so that the distal face has a smaller surface area than the proximal face. Preferably, at least a portion of an inner cavity surface is parallel with the non-beveled portions of the longitudinal walls of the housing. The inner cavity preferably comprises an inner cavity surface, a distally positioned opening, and a proximal positioned opening. In some specific embodiments, the inner cavity may be capable of containing portions of more than one wire, and portions of the inner cavity surface may not be parallel with the non-beveled portions of the longitudinal walls of the housing. For example, the inner cavity may be capable of containing a jamming lock wire as well as a guide wire, and a portion of the inner cavity may be angled to direct the jamming lock wire radially against the guide wire. In some specific embodiments, the inner cavity may not be concentric with the housing, but may be positioned closer to one side of the longitudinal walls of the housing. For example, an inner cavity that is capable of containing a braided locking wire and guide wire may not be concentric with the housing.

The terms "proximal" and "distal" are terms that are used in the same context to describe the orientation and/or movement of the angiotip, guide wire, device, catheters, sheaths, vessels, and various specific embodiments of locking wires relative to one another and a point of origin. The terms "proximal" and "distal" are terms relative to one another based on their positions relative to a point of origin or a defined reference point. The term "distal" is defined as any point farther from the point of origin or other reference point than a "proximal" point. The term "proximal" is defined as any point closer to the point of origin or other reference point than a "distal" point. The point where the angiotip is to be introduced to the body or has been introduced to the body may act as a point of origin when no other reference point is defined.

The term "inner cavity" is broadly defined herein as any open cavity or other open area located within a structure (e.g. an angiotip). Preferably, an inner cavity has two openings through the structure to the surrounding environment, and the path between the two openings is or is capable of being substantially unobstructed. An example of an inner cavity includes a channel. An inner cavity is capable of containing a length of wire such that the wire may move freely through the openings and within the inner cavity. In some specific embodiments, an inner cavity may also contain elements necessary for applying a frictional force on a wire, but the wire may still be capable of moving freely within the inner cavity. For example, a twisting lock may be housed within an inner cavity, but a wire may still pass freely through the inner cavity. Alternatively, an inner cavity of a housing may be comprised of a twisting lock and an inner cavity surface of the housing. In some specific embodiments, an inner cavity comprises an inner cavity surface with a single, edgeless, cylindrical face which directly connects the openings. In some specific embodiments, an inner cavity may comprise an inner cavity surface with multiple faces that abut in a way to directly connect the openings. For example, one of the faces may be a face angled toward one of the openings so when a wire presses against the face, it is directed towards the opening.

The term "frictionally engaging" is broadly defined herein as causing any direct or indirect physical contact between two structures or surfaces and preferably resulting in some resistance to movement of either structure or surface. Preferably, the resistance to movement is caused by the pressing of one surface against another, so when one surface is pressed against another surface, the two surfaces are frictionally engaged. In some specific embodiments, a wire may press against a housing to limit the independent movement of both the wire and the housing. In some specific embodiments, a lock that is positioned within and coupled to the housing may press against a wire, such that the lock is directly frictionally engaging the wire. In this situation, the housing and the wire are also frictionally engaged, by nature of the lock being coupled to and positioned within the housing.

The term "pressing" is broadly defined herein as an exerting of physical force upon an object. A pressing force does not need to be unidirectional or involve direct physical contact between one object and another object that is pressed. In some specific embodiments, an object may be sandwiched between two other objects, such than pressing upon one of the outer objects causes the middle object to press upon the other outer object. In some specific embodiments, pressing may be caused by two adjacent objects being positioned within a housing that has an inner cavity portion that is smaller than the size of the two objects together. In some specific embodiments, one object may encounter an angled surface that directs the object to press against another object. In some specific embodiments, a first object that encircles a second object may contract around the second object to press against it from all sides.

The term "wire" is broadly defined herein as an elongated (preferably tubular) member that is flexible and capable of being bent by human hands to a substantial degree (e.g., at least 30°) without breaking. Preferably, such a wire comprises steel and is capable of navigating through tortuous blood vessels without breaking Preferably, such a wire is between 0.012 inches and 0.038 inches in diameter. In some specific embodiments, a preferred wire size is 0.018 inches in diameter. In some specific embodiments, a preferred wire size is 0.035 inches in diameter. In some specific embodiments, the preferred wire size is 0.012 inches in diameter. In some specific embodiments, the preferred wire size is 0.014 inches in diameter. The word "first" is used only to differentiate one flexible wire from another flexible wire and should not be interpreted as defining a limitation on order or position of two wires. As is well known in the art, a wire initially introduced into the body may be replaced by other wires, any of which may be referred to as the "first flexible wire" of the claims if an angiotip is subsequently slid along it. Similarly, a "second flexible wire" simply refers to another wire besides the first flexible wire. The word "second" is used only to differentiate one flexible wire from another flexible wire and should not be interpreted as defining a limitation on order or position. A first flexible wire may be strong enough to pull an object's weight through a vessel as well as withstanding the frictional forces between the object and the vessel. Depending on its context, the term "wire" may refer to an entire wire, e.g. from one end of the wire to the other end, or to a portion of an entire wire, e.g. from a distal point of the wire to a proximal point.

The term "guide wire" is broadly defined herein as any wire capable of supporting objects which may be directed along at least a portion of its length. Preferably, a guide wire is capable of being used to navigate hollow objects through tortuous blood vessels. A guide wire may be positioned to run through a designated target site and may be capable of navigating hollow objects along at least a portion of its length to the target site.

The term "coupled to" is broadly defined herein as being integral with (part of) or being directly or indirectly attached to. Preferably, a first object coupled to a second object will cause the two objects to move as a single unit. In some specific embodiments, an angiotip may be coupled to a brake so that applying the brake to a wire results in frictional engagement of the brake with the wire, as well as frictional engagement of the angiotip with the wire. In some specific embodiments, a proximal lock may be used to couple an angiotip to a cardiovascular device, so as to cause the angiotip and cardiovascular device to move as a single unit.

The term "limiting the movement" is broadly defined herein as reducing or eliminating an object's capability to move relative to another object. Preferably, movement relative to a second object is eliminated; however, in some specific embodiments, movement relative to a second object may be reduced, such that movement of the first object relative to the second object takes more force to traverse a particular distance than force required to move the same distance prior to the limiting of the first object. For example, frictionally engaging an angiotip with a guide wire may limit movement of the angiotip relative to the guide wire, so that movement of the 2 objects is no longer independent.

The term "brake" is broadly defined herein as any structure that qualifies as a "brake" in the field of mechanics (see www.dictionary.com). Preferably, the brake referenced in the claims is capable of physically interacting with another object to directly, indirectly, or both indirectly and directly create a frictional force on the other object, e.g. on its surface. In some specific embodiments, a brake is a second wire introduced into an inner cavity of a housing with a first wire, wherein a portion of the inner cavity has an angled surface that directs the second wire against the first wire. In this situation, the second wire directly creates a frictional force between the surfaces of the first and second wires; the second wire also indirectly creates a frictional force by the second wire pressing the first wire against the inner cavity surface of the housing, thus creating friction directly between the first wire and the inner cavity surface. In some specific embodiments, a brake may be a second wire introduced into an inner cavity of a housing with a first wire, wherein the second wire is capable of being expanded to press against the first wire. In this situation, the second wire directly creates a frictional force between the surfaces of the first and second wires; the second wire also indirectly creates a frictional force by the second wire pressing the first wire against the inner cavity surface of the housing, thus creating friction directly between the first wire and the inner cavity surface. In some specific embodiments, a brake may be a twisting lock coupled to a housing that surrounds a wire, wherein the twisting lock is capable of pressing against the wire from all sides. In this situation, the twisting lock directly creates a frictional force between the twisting lock and the wire. In some specific embodiments, a brake may be a cam lock positioned within a housing, wherein the cam lock may be actuated to press a wire against the inner cavity surface of the housing. In this situation, the cam lock directly creates a frictional force between the surfaces of the cam lock and wire; the cam lock also indirectly creates a frictional force by the cam lock pressing the wire against the inner cavity surface of the housing, thus creating friction between the wire and the inner cavity surface.

The term "cardiovascular device" is broadly defined herein as any object that can be used as a tool in cardiovascular surgery for treatment, diagnostics, or exploration. The object may remain in the body after the surgery or may be removed subsequent to its use. Examples of cardiovascular devices include vascular endografts, transcatheter aortic valves, stents, balloons, tools for use in an atherectomy, intravascular imaging systems and other devices that are well known in the art.

The term "disposing against" is broadly defined herein as placing an object adjacent to and in direct or indirect physical contact with another object, such that the first object can be pressed against the other object. For example, a first wire may be disposed against a second wire so that the two wires are in direct contact with one another within an inner cavity of a housing. Preferably, by disposing the first wire against the second wire, the second wire may be directed to press against the inner cavity surface of the housing.

The term "twisting lock" is broadly defined herein as any structure capable of being rotated clockwise or counterclockwise around its axis to cause its inner diameter, e.g. of a compressed gasket, to contract. Contraction of the inner diameter of the structure may result in the pressing of an inner diameter surface against an object that resides inside the inner diameter of the structure. The structure may then be rotated in the opposite direction to dilate the inner diameter to its previous size and release the pressure on the object that may have resided within the inner diameter.

The term "blood vessel" is broadly defined herein as any elongated structure positioned within an organism comprising a lumen whose primary function is transporting blood cells. A blood vessel may be branched. A blood vessel comprises a vessel distal end and a vessel proximal end which are described relative to one another and relative to a point of origin. The vessel distal end refers to the portion of the blood vessel further from a device's point of entry in the blood vessel lumen than the vessel proximal end.

The term "proximal lock" is broadly defined herein as any lock device, preferably one capable of coupling together independent parts of a cardiovascular delivery system. In some specific embodiments, a proximal lock is capable of preventing accidental deployment of a cardiovascular device from within its sheath, catheter, or other containing structure. A proximal lock may be positioned along a wire outside the body. Alternatively, a proximal lock may be positioned along a wire within the body at a location proximal to an angiotip.

3. Certain Specific Embodiments

Now, certain specific embodiments are described, which are by no means an exclusive description of the "invention." Other specific embodiments, including those referenced in the drawings, are encompassed by this application, and any patent that issues therefrom.

One or more specific embodiments disclosed herein includes a vascular method preferably comprising: introducing a first flexible wire into a blood vessel, wherein the blood vessel has a first vessel end and a second vessel end and wherein the first flexible wire has a first end and a second end; sliding an angiotip along the first flexible wire in a direction away from the first end of the wire and toward the second end of the wire; frictionally engaging the first flexible wire with the angiotip; and pulling the first flexible wire through the blood vessel in the direction of the second vessel end, wherein the pulling of the first flexible wire pulls the angiotip through the blood vessel in the direction of the second vessel end.

In any of the methods or structures disclosed herein, the first flexible wire's first end is preferably a proximal wire end, and the first flexible wire's second end is preferably a distal wire end.

In any of the methods or structures disclosed herein, the angiotip preferably has an inner cavity and an inner cavity surface.

In any of the methods or structures disclosed herein, the first flexible wire is preferably a guide wire.

In any of the methods or structures disclosed herein, the first flexible wire preferably has a diameter ranging from 0.014 inches to 0.038 inches.

In any of the methods or structures disclosed herein, a vascular device is preferably introduced into the blood vessel.

In any of the methods or structures disclosed herein, the vascular device is preferably capable of being coupled to the angiotip by a proximal lock.

In any of the methods or structures disclosed herein, frictionally engaging the first flexible wire with the angiotip preferably includes pressing together the first flexible wire and the inner cavity surface.

In any of the methods or structures disclosed herein, the angiotip preferably has an inner cavity and an inner cavity surface, the first flexible wire preferably includes a first wire portion disposed within the inner cavity, a second flexible wire is preferably introduced to the inner cavity of the angiotip, and frictionally engaging the first flexible wire with the angiotip preferably includes disposing the second flexible wire against the first flexible wire to cause the first wire portion to press against the inner cavity surface.

One or more specific embodiments disclosed herein includes a surgical method preferably comprising: introducing a first flexible wire into a blood vessel, wherein the blood vessel has a first vessel end and a second vessel end and wherein the first flexible wire has a first end and a second end; sliding an angiotip along the first flexible wire in a direction away from the first end of the wire and toward the second end of the wire; applying a brake to the first flexible wire; and pulling the first flexible wire through the blood vessel in the direction of the second vessel end, wherein the pulling of the first flexible wire pulls the angiotip through the blood vessel in the direction of the second vessel end.

In any of the methods or structures disclosed herein, the angiotip preferably has an inner cavity and an inner cavity surface, and applying the brake to the first flexible wire preferably causes the first flexible wire to press against the inner cavity surface of the angiotip.

In any of the methods or structures disclosed herein, applying the brake to the first flexible wire preferably includes causing the brake to press circumferentially against the first flexible wire.

In any of the methods or structures disclosed herein, the angiotip preferably has an inner cavity and an inner cavity surface, the brake is preferably a second flexible wire, and applying the brake to the first flexible wire preferably includes disposing the second flexible wire against the first flexible wire to cause the first wire portion to press against the inner cavity surface.

In any of the methods or structures disclosed herein, the brake is preferably applied to the first flexible wire within the angiotip.

One or more specific embodiments disclosed herein includes a surgical device preferably comprising: a first flexible wire; an angiotip comprising an inner cavity; and a brake capable of limiting the movement of the first flexible wire in the longitudinal directions within the inner cavity of the angiotip.

In any of the methods or structures disclosed herein, the angiotip preferably includes at least one proximal opening and at least one distal opening through which the first flexible wire is capable of passing.

In any of the methods or structures disclosed herein, the angiotip preferably has an inner cavity surface, and the brake is preferably capable of pressing the first flexible wire against the inner cavity surface of the angiotip.

In any of the methods or structures disclosed herein, the angiotip preferably has an inner cavity surface, and the brake preferably comprises a second flexible wire capable of pressing the first flexible wire against the inner cavity surface of the angiotip.

In any of the methods or structures disclosed herein, the combined diameters of the first flexible wire and the second flexible wire are preferably greater than the diameter of the inner cavity of the angiotip.

In any of the methods or structures disclosed herein, the combined diameters of the first flexible wire and the second flexible wire are preferably capable of being greater than the diameter of the inner cavity of the angiotip.

In any of the methods or structures disclosed herein, the brake preferably comprises a twisting lock disposed within the inner cavity of the angiotip, the twisting lock capable of pressing the first flexible wire.

In any of the methods or structures disclosed herein, the brake preferably comprises a second flexible wire capable of pressing against the first flexible wire.

In any of the methods or structures disclosed herein, the angiotip preferably comprises an angiotip distal end and an angiotip proximal end, the angiotip distal end preferably having a diameter less than the angiotip proximal end.

4. Specific Embodiments in the Figures

Figure 2A:
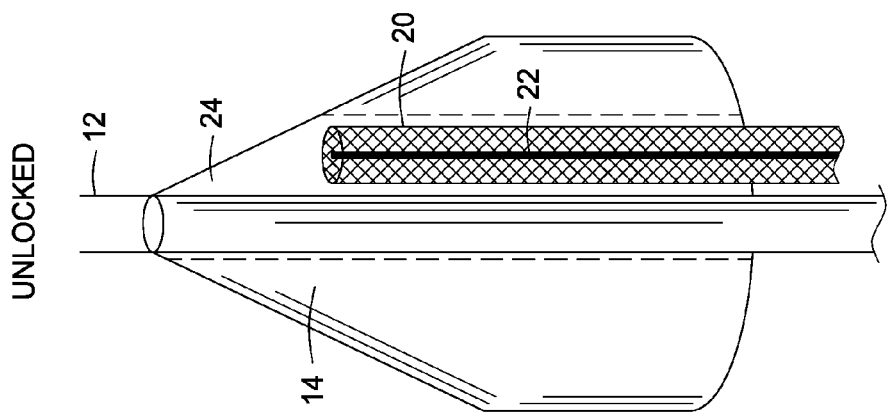
FIG. 2A is a cut-away side view of an angiotip and other elements of FIG. 1 in the unlocked position.
Figure 1:
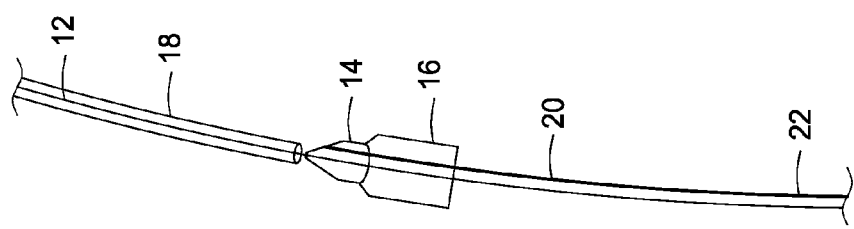
FIG. 1 is a simplified side view of several elements found in one example of an assembled vascular delivery system.

Referring to FIGS. 1, 2A, and 2B, an apparatus that includes a braided locking wire is illustrated, which has features any one of which may be found in various specific embodiments, including both those that are shown in this specification and those that are not shown.

Referring to FIG. 1, an apparatus including a braided locking wire 46 is depicted. A guide wire 12 serves as a directional device along which other surgical devices 16 may be guided through a tortuous path through the blood vessels. The guide wire 12 may be manipulated through the cardiovascular system from an entry site, through a target site, and out an exit site. An angiotip 14 may be used as a distal end for a cardiovascular device or other surgical device 16, so the diameter change of the entire system is gradual and is less likely to tear into vessel walls. The angiotip 14 may be used to guide a cardiovascular device 16 within the blood vessel. The angiotip 14 and the guide wire 12 are also capable of being frictionally engaged with each other, so that the angiotip 14 and guidewire 12 no longer move independently of one another. A braided locking wire 46 comprising a braided sheath 20 and center wire 22 is introduced to the inner cavity of the angiotip 14 when the braided sheath 20 is in its retracted state. A device such as the Lead Locking Device (LLD EZ®)

produced by Spectranetics® may be used as the braided locking wire 46 (Spectranetics® product ref 518-062). For example, the LLD EZ® device may be used in combination with a 0.018 inch guide wire 12, (such as those commercially produced by Cook Medical, Abbott Laboratories, Terumo® Medical, and Boston Scientific) so that a currently produced commercial angiotip 14 (such as those produced by Cook Medical or Endologix, Inc.) with an inner cavity diameter of 0.038 inches may be used without further modification. 14 The braided sheath 20 is capable of expanding laterally to have a larger diameter than in its retracted state. Both the braided sheath 20 and center wire 22 extend proximally from the angiotip 14 to a point outside the body near the entry site. The expanded braided sheath 20 will press the guide wire 12 against the inner cavity surface of the angiotip 14, creating friction between the guide wire 12 and the angiotip 14. A protective catheter 18 may be used to shield the vessel walls from the thin guide wire 12, as too much pressure from pulling on the guide wire 12 would otherwise lacerate the vessels at the curves of the vessels. A proximal lock 56 may be used to cause the cardiovascular device 16 and the angiotip 14 to move as a single unit in the proximal or distal direction. The proximal lock 56 may be released when the device 16 reaches the target site, so that the angiotip 14 and cardiovascular device 16 may move independently.

Referring to FIGS. 2A and 2B, an angiotip 14 comprising an inner cavity 24 is depicted. FIG. 2A shows the angiotip 14 in the "unlocked" position, where the guide wire 12 and angiotip 14 are not frictionally engaged. The guide wire 12 passes completely through the angiotip 14 with a portion of the guide wire 12 located within the inner cavity 24 of the angiotip 14. The braided locking wire 46 comprising a braided sheath 20 and center wire 22 is introduced into the proximal end of the angiotip 14 in the braided locking wire's 46 refracted state. The braided locking wire 46 has a center wire 22 that is connected to the distal end of the braided sheath 20. The center wire 22 and the braided sheath 20 can be moved together as one unit or the braided sheath 20 can be moved independently of the center wire 22 from the braided sheath proximal end 23 (See FIG. 1), causing the braided sheath 20 to expand outwardly from the center wire 22 or retract inwardly back toward the center wire 22. When the braided sheath 20 is in the retracted position, it does not apply pressure to the guide wire 12, and the guide wire 12 is capable of moving freely within the angiotip 14.

FIG. 2B shows the angiotip 14 in the "locked" position, where the guide wire 12 and the angiotip 14 are frictionally engaged by the braided locking wire 46. The proximal end of the braided sheath 20 may be advanced distally towards the angiotip 14 while the center wire 22 is held substantially in place. This will expand the diameter of the braided sheath 20 within the angiotip 14, and the expanded braided sheath 20 will press the guide wire 12 against the inner cavity surface 54 of the angiotip 14 and partially or wholly limit the longitudinal movement of the guide wire 12 within the angiotip 14. The guide wire 12 and angiotip 14 will now be moved substantially together when one or the other is moved individually.

Figure 4:
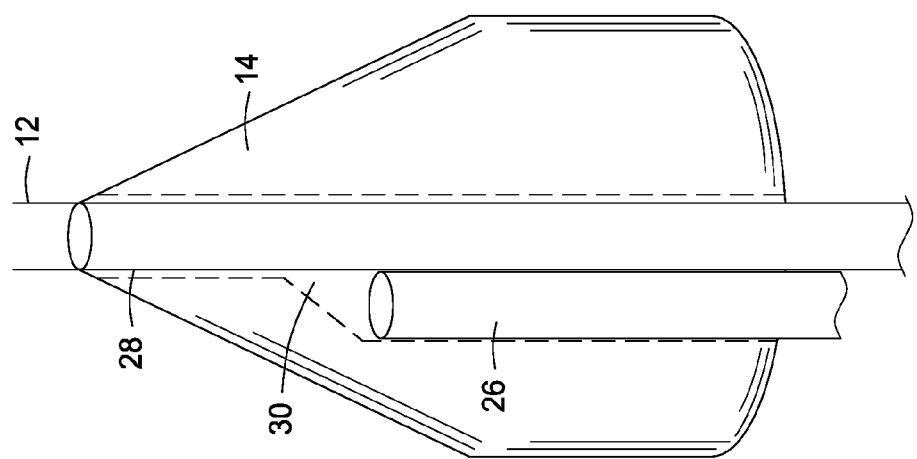
FIG. 4 is a cut-away side view of an angiotip and other elements of FIG. 3 in the unlocked position.
Figure 3:
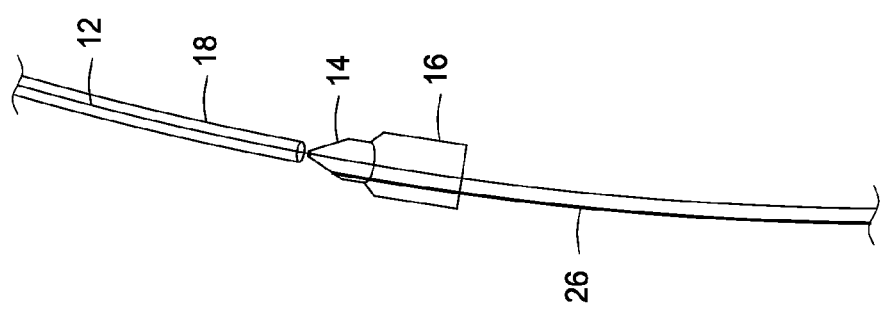
FIG. 3 is a simplified side view of several elements found in one example of an assembled vascular delivery system.

Referring to FIGS. 3 and 4, an apparatus that includes a jamming lock wire is illustrated, which has features any one of which may be found in various specific embodiments, including both those that are shown in this specification and those that are not shown.

Referring to FIG. 3, an apparatus including a jamming lock wire 26 is depicted. A guide wire 12 serves as a directional device along which other surgical devices 16 may be guided through a tortuous path through the blood vessels. The guide wire 12 is thin and may be manipulated through the cardiovascular system from an entry site, through a target site, and out an exit site. An angiotip 14 may be used as a distal end for a cardiovascular device 16 or other surgical device 16, so the diameter change of the entire system is gradual, and the device is less likely to tear into vessel walls. The angiotip 14 may be used to guide a cardiovascular device 16 within the blood vessel. The angiotip 14 and the guide wire 12 are also capable of being frictionally engaged with each other, so that the angiotip 14 and guidewire 12 no longer move independently of one another. A jamming lock wire 26 is introduced into the inner cavity of the angiotip 14. The jamming lock wire 26 extends proximally from the angiotip 14 to a point outside the body near the entry site. The jamming lock wire will press the guide wire 12 against the inner cavity surface of the angiotip 14, creating friction between the guide wire 12 and the angiotip 14. A protective catheter 18 may be used to shield the vessel walls from the thin guide wire 12, as too much pressure from pulling on the guide wire 12 may otherwise lacerate the vessels at the curves of the vessels. A proximal lock 56 may be used to cause the cardiovascular device 16 and the angiotip 14 to move as a single unit in the proximal or distal direction. The proximal lock 56 may be released when the device 16 reaches the target site so that the angiotip 14 and cardiovascular device 16 may move independently.

Referring now to FIG. 4, an angiotip 14 comprising a guide wire channel 28 and a lock wire channel 30 is depicted. A portion of guide wire 12 is disposed within the angiotip 14 while the rest of guide wire 12 extends in both the proximal and distal directions out of the angiotip 14. The jamming lock wire 26 is disposed within the angiotip 14 and extends proximally to a location out of the body so it may be accessible to the operating physician. The lock wire channel 30 may be connected to the guide wire channel 28 so that the jamming lock wire 26 passing axially through the lock wire channel 30 may also radially enter the guide wire channel 28. The guide wire channel 28 and the lock wire channel 30 may be part of a single combined inner cavity 24 that both the guide wire 12 and the jamming lock wire 26 may occupy (pictured). For example, two commercially produced wires (such as those produced by Cook Medical, Abbott Laboratories, Terumo® Medical, and Boston Scientific) whose combined diameters are equal to or slightly greater than the inner cavity diameter of a commercially produced angiotip (such as those produced by Cook Medical or Endologix, Inc.) may be used to jam both wires in place. Alternatively, there may be a divider between the two channels that is a part of the angiotip 14 (not pictured). For example, a commercially available angiotip (such as those produced by Cook Medical or Endologix, Inc.) may be modified by drilling a second channel in the angiotip for a jamming lock wire to pass through. When the jamming lock wire 26 is advanced distally and axially to the end of the lock wire channel 30, it may be directed towards the guide wire channel 28 (i.e. in a somewhat radial direction) and press against the guide wire 12. When the jamming lock wire 26 presses against the guide wire 12, friction is created between the jamming lock wire 26 and the guide wire 12, as well as between the guide wire 12 and the inner cavity surface 54 of the angiotip 14. The guide wire 12 and the angiotip 14 are now frictionally engaged and may now be moved substantially together when one or the other is moved individually, particularly in a proximal or distal (axial) direction. The frictional engagement can be released by retracting the jamming lock wire 26 in the proximal direction so that the jamming lock wire 26 no longer presses against the guide wire 12.

Figure 6B:
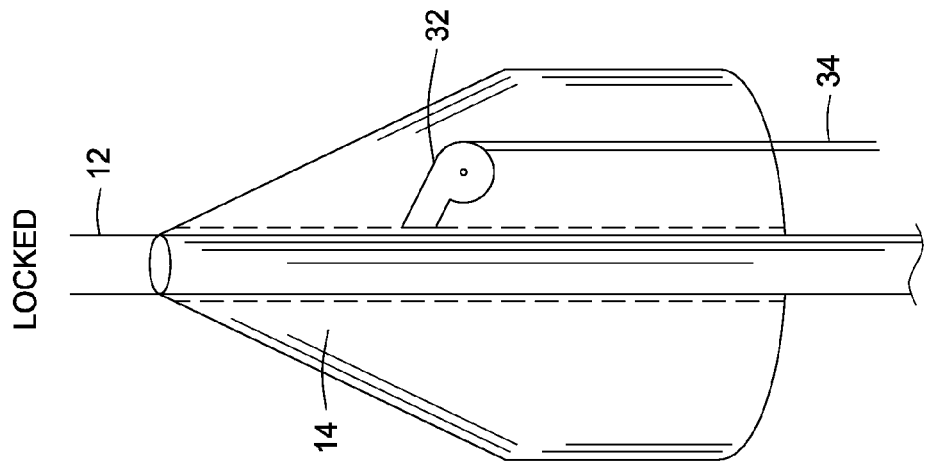
FIG. 6B is a cut-away side view of an angiotip and other elements of FIG. 5 in the locked position.
Figure 6A:
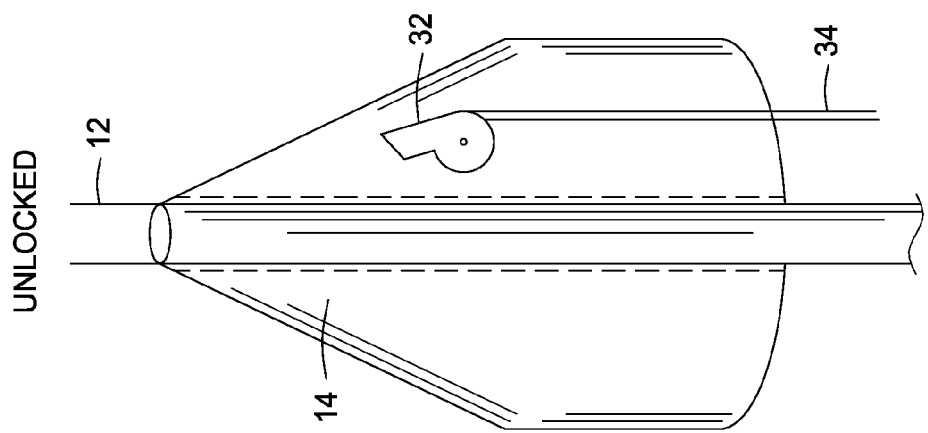
FIG. 6A is a cut-away side view of an angiotip and other elements of FIG. 5 in the unlocked position.
Figure 5:
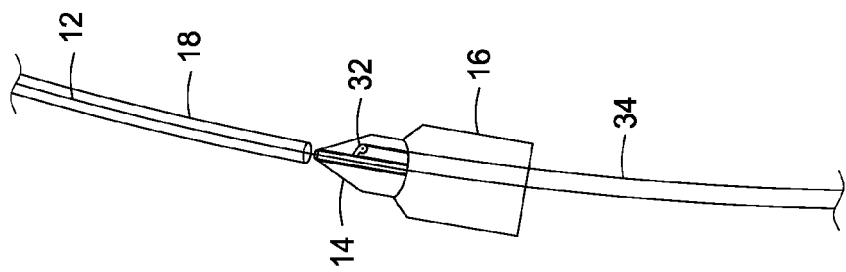
FIG. 5 is a simplified side view of several elements found in one example of an assembled vascular delivery system.

Referring to FIGS. 5, 6A, and 6B, an apparatus that includes a cam lock is illustrated, which has features any one of which may be found in various specific embodiments, including both those that are shown in this specification and those that are not shown.

Referring to FIG. 5, an apparatus including a cam lock 32 is depicted. A guide wire 12 serves as a directional device along which other surgical devices 16 may be guided through a tortuous path through the blood vessels. The guide wire 12 is thin and may be manipulated through the cardiovascular system from an entry site, through a target site, and out an exit site. An angiotip 14 may be used as a distal end for a cardiovascular device or other surgical device 16, so the diameter change of the entire system is gradual, and the device is less likely to tear into vessel walls. The angiotip 14 may be used to guide a cardiovascular device 16 within the blood vessel. The angiotip 14 and the guide wire 12 are also capable of being frictionally engaged with each other, so that the angiotip 14 and guidewire 12 no longer move independently of one another. A cam lock 32 may be positioned within the angiotip 14, preferably within the inner cavity of the angiotip 14. A cam lock wire 34 may be attached to the cam lock 32 and extend proximally from within the angiotip 14 to a point outside the body near the entry site, so it may be accessible to the operating physician. The cam lock 32 is located within the angiotip 14 and has a point of rotation. The cam lock 32 can rotate about this point so that an edge of the cam lock 32 can press radially against the guide wire 12. The rotating motion is directed by the cam lock wire 34 so that advancing the cam lock wire 34 axially in the distal direction rotates the cam lock 32 so that the cam lock 32 presses against the guide wire 12. The cam lock wire 34 may alternatively be attached to the cam lock 32 in a way that retracting the cam lock wire 34 in the proximal direction rotates the cam lock 32 so that it presses against the guide wire 12 (example diagram not depicted). A protective catheter 18 may be used to shield the vessel walls from the thin guide wire 12, as too much pressure from pulling on the guide wire 12 might otherwise lacerate the vessels at the curves of the vessels. A proximal lock 56 may be used to cause the cardiovascular device 16 and the angiotip 14 to move as a single unit in the proximal or distal direction. The proximal lock 56 may be released when the device 16 reaches the target site so that the angiotip 14 and cardiovascular device 16 may move independently.

Referring to FIGS. 6A and 6B, an angiotip 14 comprising a cam lock 32 is depicted. FIG. 6A shows the angiotip 14 in the "unlocked" position, where the guide wire 12 and angiotip 14 are not frictionally engaged. The guide wire 12 passes completely through the inner cavity 24 of the angiotip 14 with a portion of the guide wire 12 located within the inner cavity of the angiotip 14. The cam lock 32 is rotated to an angle where it does not press against the guide wire 12. The rotation of the cam lock 32 is controlled by the cam lock wire 34, so that when the cam lock wire 34 is retracted in the proximal direction, the cam lock 32 does not press the guide wire 12 against the inner cavity surface 54 (as pictured). The rotation of the cam lock 32 can alternately be controlled by the cam lock wire 34 so that when the cam lock wire 34 is advanced distally, the cam lock 32 does not press against the guide wire 12 (example not depicted). When the cam lock 32 is not pressing against the guide wire 12, the guide wire 12 is capable of moving freely within the angiotip 14.

FIG. 6B shows the angiotip 14 in the "locked" position, where the guide wire 12 and the angiotip 14 are frictionally engaged due to the cam lock 32 pressing the guidewire 12 against the inner cavity surface 54 of the angiotip 14. The rotation of the cam lock 32 is controlled by the cam lock wire 34, so that when the cam lock wire 34 is advanced in the distal direction, the cam lock 32 may press the guide wire 12 against the inner cavity surface 54 of the angiotip 14 and partially or wholly limit the longitudinal movement of the guide wire 12 within the inner cavity 24 of the angiotip 14. The cam lock 32 may press against the guide wire 12, and friction may be created between the cam lock 32 and the guide wire 12, as well as between the guide wire 12 and the inner cavity surface 54 of the angiotip 14. The guide wire 12 and angiotip 14 may now be frictionally engaged and may be moved substantially together when one or the other is moved individually.

Figure 7:
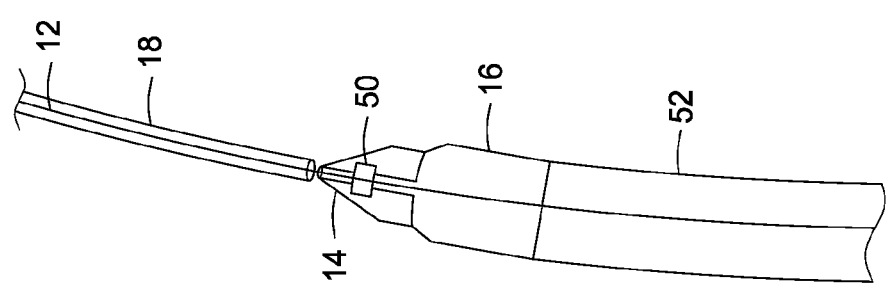
FIG. 7 is a simplified side view of several elements found in one example of an assembled vascular delivery system.
Figure 8:
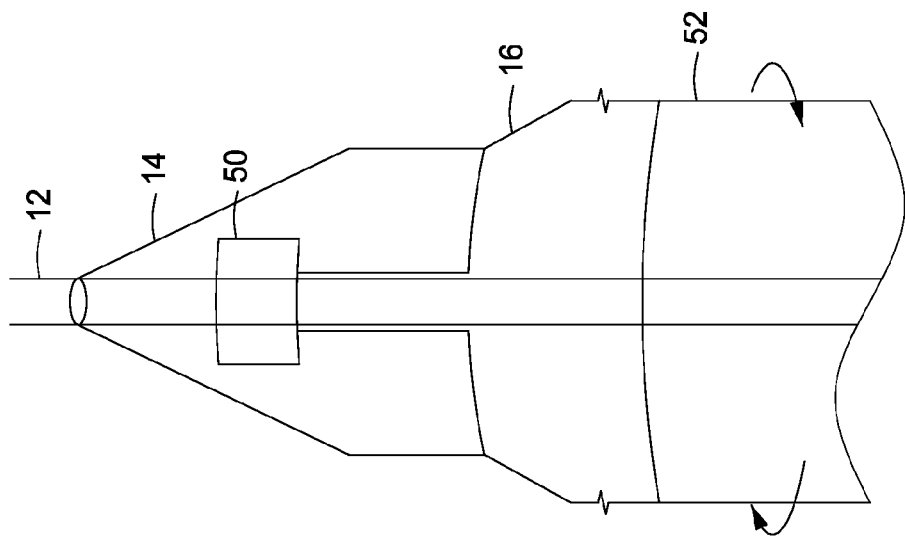
FIG. 8 is a cut-away side view of an angiotip and other elements of FIG. 7.

Referring to FIGS. 7 and 8, an apparatus that includes a twisting lock is illustrated, which has features any one of which may be found in various specific embodiments, including both those that are shown in this specification and those that are not shown.

Referring to FIG. 7, an apparatus including a twisting lock 50 is depicted. A guide wire 12 serves as a directional device along which other surgical devices 16 may be guided through a tortuous path through the blood vessels. The guide wire 12 is thin and may be manipulated through the cardiovascular system from an entry site, through a target site, and out an exit site. An angiotip 14 may be used as a distal end for a cardiovascular device or other surgical device 16, so the diameter change of the entire system is gradual, and the device is less likely to tear into vessel walls. The angiotip 14 may be used to guide a cardiovascular device 16 within the blood vessel. The angiotip 14 and the guide wire 12 are also capable of being frictionally engaged with each other, so that the angiotip 14 and guidewire 12 no longer move independently of one another. A twisting lock 50 is positioned within and coupled to the angiotip 14. The twisting lock 50 is such that when it is rotated either clockwise or counterclockwise, the inner diameter of the twisting lock 50 may decrease. The inner surface of the twisting lock 50 may then press on the guide wire 12, thus creating friction between the guide wire 12 and the twisting lock 50. The twisting lock 50 may be coupled to either the device 16 or a sheath 52, so that turning on the sheath 52 at the proximal end will turn the twisting lock 50 within the angiotip 14. The sheath 52 may extend proximally out of the body so that it may be accessible to the operating physician, coupled to another object that may extend proximally out of the body, or there may be other means of rotating the sheath 52 that are well known in the art. Alternately, there may be another device or series of devices coupled to the twisting lock 50 that extend proximally out of the body, so that rotating this device or devices also rotates the twisting lock 50 within the angiotip 14 (example not pictured). A protective catheter 18 may be used to shield the vessel walls from the thin guide wire 12, as too much pressure from pulling on the guide wire 12 would otherwise lacerate the vessels at the curves of the vessels. A proximal lock 56 may be used to cause the cardiovascular device 16 and the angiotip 14 to move as a single unit in the proximal or distal direction. The proximal lock 56 may be released when the device 16 reaches the target site so that the angiotip 14 and cardiovascular device 16 may move independently.

Referring now to FIG. 8, an angiotip 14 comprising a twisting lock 50 is depicted. The twisting lock 50 is positioned within the angiotip 14, but it is free to rotate within the angiotip 14. The twisting lock 50 is coupled to the device 16 or sheath 52, so that twisting the device 16 or sheath 52 about its longitudinal axis will also turn the twisting lock 50 about its axis. Alternately, there may be another device or series of devices coupled to the twisting lock 50 so that rotating these device(s) would also rotate the twisting lock 50 within the angiotip 14. Rotating the twisting lock 50 may cause the inner diameter of the twisting lock 50 to decrease. The inner surface of the twisting lock 50 may press on the guide wire 12. The longitudinal movement of the guide wire 12 may be limited within the angiotip 14 due to friction created between the twisting lock 50 and the guide wire 12. Once the twisting lock 50 is rotated and presses against the guide wire 12, pulling the guide wire 12 in a distal direction may now also move the angiotip 14 in a distal direction, as the twisting lock 50 is coupled to the angiotip 14. The twisting lock 50 may be turned in the opposite direction to release the pressure on the guide wire 12 to release the frictional engagement and allow the guide wire 12 to move freely through the angiotip 14.

Referring to FIGS. 9A, 9B, 9C, and 9D, the movements of several specific embodiments through the body are generally depicted in a step-wise manner.

Referring to FIG. 9A, a guide wire 12 having both a proximal end and a distal end is introduced into the body via an entrance site 36 which may be positioned on a femoral artery 44. The guide wire 12 is directed through the cardiovascular system to a location (for example, the descending aorta) that is the target site 42 of the surgery, which may be exploratory, diagnostic, or therapeutic in nature. The guide wire 12 is then directed past the target site 42 to a point distal the target location. The guide wire will then be directed out of the body via an exit site 38 which may be positioned on a brachial artery 40. Alternatively, the target site may be located within the heart (e.g. the aortic valve), the guide wire may be fed out through the heart (e.g. the apex), and the exit site may be through the left chest wall (example not pictured). The guide wire 12 may now protrude from the body in two places, at the exit site 38 and the entrance site 36. A proximal lock 56 may be positioned outside of the body near the entrance site 36 and may be used to cause the cardiovascular device 16 and the angiotip 14 to move as a single unit in the proximal or distal directions.

Referring now to FIG. 9B, an angiotip 14 is introduced into the body through the entrance site 36 by sliding the angiotip 14 along the guide wire 12. The angiotip 14 may be advanced by using a pusher rod 48 to apply force behind the angiotip 14 and direct the angiotip 14 in a distal direction towards the target site 42 and away from the entrance site 36. The guide wire 12 may be held in substantially in the same position within the body as the angiotip 14 slides along the guide wire 12. Alternatively, this step may be omitted, i.e. the angiotip 14 is not introduced into the body nor advanced using the pusher rod 48. The angiotip 14 and optional cardiovascular device 16 may be introduced into the body through the exit site 38 instead of the entrance site 36 (example diagram not pictured). In this case, the point of origin would be the exit site 38 and sliding in the distal direction would involve moving towards the target site 42 and the entrance site 36 and away from the exit site 38.

Referring now to FIG. 9C, the angiotip 14 may be positioned somewhere distal to the entrance site 36 and proximal the target site 42 and the exit site 38. The angiotip 14 may alternately be positioned still outside the body near the entrance site 36 or the exit site 38 (example diagram not pictured). A locking wire 58 is now introduced into the through entrance site 36 and up to the angiotip 14. The locking wire 58 may alternatively be introduced to the angiotip 14 when the angiotip 14 is still outside of the body (example diagram not pictured). The inner cavity 24 of the angiotip 14 now contains the guide wire 12 and the locking wire 58 placed adjacent to one another. The locking wire 58 may extend from within the angiotip 14 to a position outside of the body, so it may be accessible to the operating physician. The locking wire 58 may cause the guidewire 12 to press against the angiotip 14 in one or more of the several ways described in the specification, so that the guide wire 12 is frictionally engaged with the angiotip 14. A protective catheter 18 is introduced into the body over the guide wire 12 via the exit site 38. The protective catheter 18 is advanced in the proximal direction towards the entrance site 36 until it reaches the angiotip 14. The protective catheter 18 extends from the distal end of the angiotip 14 over the guide wire 12, exits the body at the exit site 38, and may extend over the guide wire 12 outside of the body. The protective catheter 18 is in place to prevent a "cheese cutter" effect by the guide wire 12, where too much pressure from pulling on the thin guide wire 12 might otherwise lacerate the vessels at curves in the vessels.

Referring now to FIG. 9D, the frictionally engaged guide wire 12, protective catheter 18, locking wire 58, and angiotip 14 are now capable of being pulled as a single unit from the guide wire's distal end in the distal direction. The cardiovascular device 16 may still be coupled to the angiotip 14 by the proximal lock 56. The angiotip 14 will be directed distally towards the target site 42. The cardiovascular device 16 may also be moved distally with the angiotip 14, guide wire 12, protective catheter 18, and locking wire 58. The angiotip 14 and cardiovascular device 16 may now be advanced distally to the target site 42 by pulling a portion of the guide wire 12 that is located distally from the angiotip 14, thus exerting a pulling force on the angiotip 14 where it is frictionally engaged with the guide wire 12. This pulling force may be used alone to direct the angiotip 14 and cardiovascular device 16, or in combination with a pushing force exerted at a location proximal from the angiotip 14, including from a position outside of the body near the entrance site 36. Once the angiotip 14 and cardiovascular device 16 are in place at the target site 42, the frictional engagement on the guide wire 12 and angiotip 14 may be removed by removing the pressure caused by the locking wire 58. The guide wire 12 and angiotip 14 are no longer frictionally engaged and may now be moved independently of one another. The proximal lock 56 may be removed after the cardiovascular device 16 has reached the target site, so that the angiotip 14 and the cardiovascular device 16 may now move independently of one another.

What is claimed as the invention is:

1. A vascular delivery device comprising:
  a first wire having a first proximal wire end and a first distal wire end;
  a second wire having a second proximal wire end and a second distal wire end; and
  a housing having an inner cavity, an inner cavity surface, a distal face, and a proximal face; wherein:
  the first wire is capable of being introduced into a blood vessel having a distal vessel end and a proximal vessel end by sliding over a second wire;
  the first wire is capable of being introduced into the inner cavity of the housing;
  at least a portion of the first wire is capable of expanding within the inner cavity of the housing to provide an expanded portion of the first wire such that the expanded portion of the first wire makes contact with the inner cavity surface of the housing and the second wire and restricts longitudinal movement of the second wire with respect to the housing;
  the second wire is capable of being frictionally engaged with the housing by causing the portion of the first wire to expand within the inner cavity of the housing such that the portion of the first wire contacts both the second wire and the inner cavity surface of the housing and restricts longitudinal movement of the second wire with respect to the housing;
  the second wire is a guide wire;

the second wire is capable of being pulled through the blood vessel in the direction of the distal vessel end; and pulling of the second wire pulls the housing through the blood vessel in the direction of the distal vessel end.

2. A vascular delivery device comprising:

a first wire having a first proximal wire end and a first distal wire end;

a second wire having a second proximal wire end and a second distal wire end; and a housing having an inner cavity, an inner cavity surface, a distal housing end, and a proximal housing end; wherein:

the housing is capable of sliding along the second wire in a direction away from the second proximal wire end and toward the second distal wire end;

the housing is beveled such that the distal housing end has a smaller surface area than the proximal housing end;

the first wire is capable of being introduced into the inner cavity of the housing by passing the first distal wire end into a blood vessel having a proximal vessel end and a distal vessel end through an opening nearer to the proximal vessel end than the distal vessel end such that at least a portion of the first distal wire end is positioned within the inner cavity of the housing, the second wire is capable of being frictionally engaged with the housing by causing at least a portion of the first wire to expand within the inner cavity of the housing such that the portion of the first wire contacts the second wire and the inner cavity surface of the housing and restricts longitudinal movement of the second wire with respect to the housing; and the second wire is capable of being pulled through the blood vessel in the direction of the distal vessel end, wherein pulling of the second wire pulls the housing through the blood vessel in the direction of the distal vessel end.

3. A vascular delivery device comprising:

a first wire having a first proximal wire end and a first distal wire end;

a second wire having a second proximal wire end and a second distal wire end;

a housing having an inner cavity, an inner cavity surface, a distal housing end, and a proximal housing end; and a cardiovascular device coupled to the housing; wherein:

the housing is capable of sliding along the second wire in a direction away from the second proximal wire end and toward the second distal wire end;

the first wire is capable of being introduced into the inner cavity of the housing by passing the first distal wire end into a blood vessel having a proximal vessel end and a distal vessel end through an opening nearer to the proximal vessel end than the distal vessel end such that at least a portion of the first distal wire end is positioned within the inner cavity of the housing, the second wire is capable of being frictionally engaged with the housing by causing at least a portion of the first wire to expand within the inner cavity of the housing such that the portion of the first wire contacts the second wire and the inner cavity surface of the housing and restricts longitudinal movement of the second wire with respect to the housing;

the second wire is capable of being pulled through the blood vessel in the direction of the distal vessel end, wherein pulling of the second wire pulls the housing through the blood vessel in the direction of the distal vessel end; and the cardiovascular device is capable of uncoupling from the housing and capable of being deployed.

4. A vascular delivery device comprising:

a first wire having a first proximal wire end and a first distal wire end;

a second wire having a second proximal wire end and a second distal wire end;

a cardiovascular device; and a housing having an inner cavity, an inner cavity surface, a distal face, and a proximal face; wherein:

the first wire is capable of being introduced into a blood vessel by sliding over a second wire;

the first wire is capable of being introduced into the inner cavity of the housing;

at least a portion of the first wire is capable of expanding within the inner cavity of the housing to provide an expanded portion of the first wire such that the expanded portion of the first wire makes contact with the inner cavity surface of the housing and the second wire and restricts longitudinal movement of the second wire with respect to the housing;

the second wire is capable of being frictionally engaged with the housing by causing the portion of the first wire to expand within the inner cavity of the housing such that the portion of the first wire contacts both the second wire and the inner cavity surface of the housing and restricts longitudinal movement of the second wire with respect to the housing;

the second wire is a guide wire; and the first wire, the second wire, the housing, and the cardiovascular device are capable of being pulled as a single unit from the second distal wire end in a distal direction when the second wire is frictionally engaged with the housing.

* * * * *